United States Patent
Hyun et al.

(10) Patent No.: US 7,405,817 B2
(45) Date of Patent: Jul. 29, 2008

(54) METHOD AND APPARATUS FOR CLASSIFYING DEFECTS OF AN OBJECT

(75) Inventors: Pil-Sik Hyun, Suwon-si (KR);
Sun-Yong Choi, Sungnam-si (KR);
Sang-Kil Lee, Yongin-si (KR);
Chung-Sam Jun, Suwon-si (KR);
Sang-Min Kim, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 316 days.

(21) Appl. No.: 10/786,137

(22) Filed: Feb. 26, 2004

(65) Prior Publication Data

US 2005/0018182 A1    Jan. 27, 2005

(30) Foreign Application Priority Data

Feb. 26, 2003    (KR)    ................. 2003-12088

(51) Int. Cl.
*G01N 21/00* (2006.01)
*G01J 4/00* (2006.01)

(52) U.S. Cl. .................. 356/237.5; 356/237.4; 356/369

(58) Field of Classification Search .............. 356/237.1, 356/237.4, 495, 511, 237.5, 364, 369
See application file for complete search history.

(56) References Cited

U.S. PATENT DOCUMENTS

| | | | |
|---|---|---|---|
| 5,936,726 A | 8/1999 | Takeda et al. | |
| 6,169,601 B1 | 1/2001 | Eremin et al. | |
| 6,411,377 B1 * | 6/2002 | Noguchi et al. | 356/237.4 |
| 6,760,100 B2 * | 7/2004 | Ivakhnenko et al. | 356/237.2 |
| 6,888,627 B2 * | 5/2005 | Leslie et al. | 356/237.2 |
| 6,897,957 B2 * | 5/2005 | Meeks | 356/430 |

FOREIGN PATENT DOCUMENTS

| | | |
|---|---|---|
| EP | 0 887 621 | 12/1998 |
| KR | 10-0245805 | 8/1998 |
| KR | 2000-0064554 | 11/2000 |

\* cited by examiner

*Primary Examiner*—Hwa (Andrew) S Lee
(74) *Attorney, Agent, or Firm*—Lee & Morse, P.C.

(57) ABSTRACT

A method for classifying defects of an object includes irradiating lights having different polarizations onto the object to create an inspection spot on the object, collecting scattered lights generated by the irradiated lights scattering from the inspection spot, and classifying defects of the object by type of defect by analyzing the scattered lights. An apparatus for classifying defects of an object includes light creating means emitting lights having different polarizations to create an inspection spot on the object, and a detecting member for collecting scattered lights that are created from the lights scattering from the inspection spot, wherein the scattered lights are analyzed and classified in accordance with defects positioned on the inspection spot of the object.

43 Claims, 17 Drawing Sheets

METHOD AND APPARATUS FOR CLASSIFYING DEFECTS OF AN OBJECT

BACKGROUND OF THE INVENTION

1. Field of the Invention

The present invention relates to a method and an apparatus for classifying defects of an object. More particularly, the present invention relates to a method and an apparatus for rapidly inspecting and classifying defects, such as particles or scratches, of an object, such as a wafer.

2. Description of the Related Art

A semiconductor fabricating process indispensably requires a process for inspecting defects of an object, such as a wafer. For example, after forming fine patterns on the wafer using a photolithography process, defects, such as particles or micro-scratches, may be generated on the pattern formed on the wafer. In addition, when a chemical mechanical polishing (CMP) process is performed on the wafer including the patterns, additional defects may be generated on the pattern formed on the wafer.

Conventional inspection equipment may inspect only whether defects are present on the patterns. Conventionally, an inspector directly identifies defects either by the naked eye or by using an additional review tool.

As inspection equipment has rapidly improved, an ability to manage scores of defects has improved to an ability to manage hundreds or thousands of defects. At the same time, the time and the effort for classifying the defects have remarkably increased. This increase in time and effort decreases a productivity of a semiconductor device. To prevent this decrease in the productivity of the semiconductor device, the inspection process is only performed on selected portions of the wafers. However, this selective inspection causes another problem in that a reliability of the inspection process may be lowered. Accordingly, a method and an apparatus for fast and efficient classification of defects are in demand.

FIG. 1 is a flow chart illustrating a conventional method for classifying defects of a wafer.

Referring to FIG. 1, in step S11, a surface of a wafer is scanned using defect inspecting equipment. In step S12, the defect inspecting equipment obtains information concerning the number and coordinates of defects generated on the wafer. In step S13, a server stores this information from the defect inspecting equipment.

In step S14, it is determined whether the number of defects exceeds a count specification. If the number of the defects on the wafer exceeds the count specification, a semiconductor fabricating process will be suspended due to a "spec out interlock" thereof. Subsequently, in step S15, the wafer is transferred to a review tool and is reviewed. Here, the review process represents a process that identifies the shape and formation of the defects on the wafer by an inspector using the review tool in accordance with the information concerning the defects. The review tool may be a microscope or a scanning electron microscope (SEM).

In step S16, the review process determines whether the extent to which defects on the wafer may affect the semiconductor manufacturing processes. In particular, it is determined whether the defects exceed a critical defect specification. If the defects on the wafer exceed the critical defect specification, in step S17, the semiconductor fabricating process is suspended due to a "spec out interlock" thereof.

If the number of defects fails to exceed the count specification in step S14 or the defects fail to exceed the critical defect specification in step S16, then, in step S18, subsequent semiconductor manufacturing processes are advanced.

FIGS. 2A and 2B are graphs illustrating results of a conventional method for classifying defects according to a manual review process.

Referring to FIG. 2A, when a number of defects detected exceeds a reference number, for example, about 200, the wafer is reviewed to determine whether further processes should be suspended or advanced.

In the review process, a worker, i.e., the inspector, visually inspects the defects on the wafer. The worker manually classifies the types of the defects, and then inputs the information concerning the classified defects onto a server, where the information is stored. Types of stored defects may be classified as shown in FIG. 2B. Specifically, a type I defect corresponds to a critical defect, from among type I to type IV defects. The number of type I defects may determine whether further processes are suspended or advanced. For example, type I defects indicate particles, type II defects represent flat defects, type III defects indicate contact recesses, and type IV defects represent scratches.

Since a conventional inspecting apparatus determines the review process in accordance with the total number of the defects on the wafer, the conventional inspecting apparatus may not discriminate between severity or types of the defects when the total number of the defects is below a reference number, even if all of the defects are of the most severe variety. As a practical matter, this often occurs in semiconductor manufacturing processes. Here, the reference number of the defects may be properly adjusted in the processes after the occurrence.

Particularly, when the number of the defects is in a range of about hundreds to thousands, a problem occurs in that not all of the defects may be classified because a time of the review process may be prohibitively long.

Furthermore, the classification of the defects through manual review may lack objectivity in view of the subjective judgment of the inspector. For example, the conventional inspecting apparatus inspects about 200 to about 300 wafers per day. The number of wafers inspected per day in one fabricating line using seven inspecting apparatuses is about 1,400 to about 2,100. Thus, only a small number of wafers are actually reviewed among the inspected wafers.

To overcome the problems caused by manual inspection, there is disclosed an auto defect classification (ADC). A method according to the ADC includes inspecting the defects on the wafer, determining coordinates of the defects, verifying images of the defects stored in the server and classifying the defects. The classification can be automatically performed in the ADC. However, the ADC may be practically employed in the present because the inspecting time of the ADC is much longer than that of the manual inspection and also initial conditions may not be easily set in the ADC.

SUMMARY OF THE INVENTION

The present invention provides a method for classifying defects that is able to provide reliable information concerning all of the defects on an object and reduce unnecessary review time.

The present invention provides an apparatus for classifying defects that is able to provide reliable information concerning all of the defects on an object and reduce unnecessary review time.

In accordance with a feature of an embodiment of the present invention, a method for classifying defects of an object includes irradiating lights having different polarizations onto the object to create an inspection spot on the object, collecting scattered lights generated by the irradiated lights scattering from the inspection spot, and classifying defects of the object by type of defect by analyzing the scattered lights. In the method, irradiating lights having different polarizations may include irradiating a first light and a second light onto the inspection spot, wherein a first scattered light and a second scattered light are generated by the first light and the second light, respectively, scattering from the inspection spot. Irradiating the first light and the second light may further include generating a first polarized light and a second polarized light from the first light and the second light, respectively, using a polarizer, wherein the first polarized light and the second polarized light are irradiated onto the inspection spot. The first polarized light and the second polarized light may be two different lights selected from the group consisting of a primary polarized (P) light, a secondary polarized (S) light and a circular polarized (C) light. The first light may be positioned opposite to the second light.

The method may further include providing a first light source for emitting the first light and providing a second light source for emitting the second light, wherein the second light source is positioned opposite to the first light source.

Irradiating the first light and the second light onto the inspection spot may include irradiating a main light from a light source and generating the first light and the second light from the main light.

In the method, the first light may be directly generated from a first portion of the main light, and the second light may be generated by changing a path of a second portion of the main light.

The method may further include providing a light path changing member including a first mirror passing the first portion of the main light to generate the first light and reflecting the second light to a second mirror, the second mirror reflecting the second light to a third mirror, the second mirror corresponding to the first mirror, the third mirror reflecting the second light to a fourth mirror, the third mirror being opposed to the second mirror, and the fourth mirror reflecting the second light onto the inspection spot, the fourth mirror being opposed to the first mirror and corresponding to the third mirror, wherein the first light and the second light are generated from the main light using the light path changing member, and the second light is irradiated onto the inspection spot by being reflected from the first, second, third, and fourth mirrors. Here, the second light passing the light path changing member may be irradiated onto the inspection spot from a direction opposite to the direction from which the first light is irradiated onto the inspection spot.

In the method, a first polarized light and a second polarized light may be generated using polarizers disposed on paths of the first light and the second light, respectively, and the first polarized light and the second polarized light may be two different lights selected from the group consisting of a primary polarized (P) light, a secondary polarized (S) light and a circular polarized (C) light.

Irradiating the lights and collecting the scattered lights may be subsequently performed.

The lights having different polarizations may be generated from a single light source. The lights may be irradiated onto an incident face of the object at an angle of about 1020 to about 30°. The scattered lights may be collected at an angle in a range of about 40° to about 50° relative to irradiation directions of the lights with reference to the inspection spot.

In the method, classifying the defects includes comparing combinations of scattering values of the scattered lights to predetermined reference values and defining the defects of the inspection spot in accordance with types of the defects corresponding to the reference values. Here, the method may further include defining sample values by inspecting the defects of the object, wherein the defects are classified by comparing the defined sample values to the scattering values.

The method may further include identifying a defect having a specific type from all of the defects.

In accordance with another feature of an embodiment of the present invention, an apparatus for classifying defects of an object includes light creating means emitting lights having different polarizations to create an inspection spot on the object and a detecting member for collecting scattered lights that are created from the lights scattering from the inspection spot, wherein the scattered lights are analyzed and classified in accordance with defects positioned on the inspection spot of the object.

The light creating means may include a light source and a polarizer disposed on a path of the lights between the light source and the inspection spot to create polarized lights and to control characteristics of the polarized lights. Here, the polarizer generates one selected from the group consisting of a primary polarized (P) light, a secondary polarized (S) light and a circular polarized (C) light. The polarizer may include plates of about a ½ wavelength and about a ¼ wavelength corresponding to the lights to create the polarized lights by combining the plates.

In the apparatus, the light creating means may include at least one laser source for irradiating the lights onto the object within a range of angles of about 10° to about 30°. The detecting member may include at least one detector disposed above a surface of the object within a range of angles of about 40° to about 50° relative to directions of the lights with respect to the inspection spot.

In accordance with still another feature of an embodiment of the present invention, a method for classifying defects of an object includes irradiating a first light onto the object to create an inspections spot on the object, collecting a first scattered light created by the first light scattering from the inspection spot using a first detector, irradiating a second light to the inspection spot, collecting a second scattered light created by the second light scattering from the inspection spot using a second detector, and classifying defects on the object by type of defect by analyzing the first scattered light and the second scattered light.

In the method, the first light and the second light may be oppositely irradiated onto the inspection spot within a range of angles of about 10° to about 30°. The first scattered light and the second scattered light may be collected within a range of angles of about 40° to about 50° relative to irradiating directions of the first light and the second light with respect to the inspection spot. The first polarized light and the second polarized light may be two different lights selected from the group consisting of a primary polarized (P) light, a secondary polarized (S) light and a circular polarized (C) light.

In accordance with yet another feature of an embodiment of the present invention, an apparatus for classifying defects of an object includes a first light source irradiating a first light onto the object for creating an inspection spot on the object, a first detector collecting a first scattered light that is created from the first light scattering from the inspection spot, a second light source irradiating a second light onto the inspection spot, and a second detector collecting a second scattered light that is created from the second light scattering from the inspection spot, wherein the first and second scattered lights are analyzed and classified according to defects positioned on the inspection spot of the object.

In the apparatus, the first light source and the second light source may be disposed opposite with each other with respect to the inspection spot to irradiate the first light and the second light to the object within a range of angles of about 10° to about 30°. The first detector and the second detector may be disposed above a surface of the object within a range of angles of about 40° to about 50° relative to directions of the lights on the basis of the inspection spot.

The apparatus may further include a first polarizer disposed on a path of the first light and including plates of about a ½ wavelength and about a ¼ wavelength to generate one selected from the group consisting of a primary polarized (P) light, a secondary polarized (S) light and a circular polarized (C) light from the first light and a second polarizer disposed on a path of the second light and including plates of about a ½ wavelength and about a ¼ wavelength to generate one selected from the group consisting of a primary polarized (P) light, a secondary polarized (S) light and a circular polarized (C) light from the second light.

In accordance with yet still another feature of an embodiment of the present invention, a method for classifying defects of an object includes irradiating a main light onto the object to create an inspections spot on the object, creating a first light and a second light by splitting the main light, collecting a first scattered light created by the first light scattering from the inspection spot using a first detector, collecting a second scattered light created by the second light scattering from the inspection spot using a second detector, and classifying defects on the object by type of defect by analyzing the first scattered light and the second scattered light.

The method may further include providing a light path changing member including a first mirror passing the first portion of the main light to generate the first light and reflecting the second light to a second mirror, the second mirror reflecting the second light to a third mirror, the second mirror corresponding to the first mirror, the third mirror reflecting the second light to a fourth mirror, the third mirror being opposed to the second mirror, and the fourth mirror reflecting the second light onto the inspection spot, the fourth mirror being opposed to the first mirror and corresponding to the third mirror, wherein the first light and the second light are generated from the main light using the light path changing member, and the second light is irradiated onto the inspection spot by being reflected from the first, second, third, and fourth mirrors.

In the method, a first polarized light and a second polarized light are created using polarizers disposed on a path of the first light and on a path of the second light, respectively, wherein the first polarized light and the second polarized light are two different lights selected from the group consisting of a primary polarized (P) light, a secondary polarized (S) light and a circular polarized (C) light.

In accordance with still another feature of an embodiment of the present invention, an apparatus for classifying defects of an object includes a light source irradiating a main light onto the object for creating an inspection spot on the object, a light path changing member creating a first light by passing therethrough a first portion of the main light and a second light by changing a path of a second portion of the main light, and directing a path of the second light to the inspection spot, a first detector collecting a first scattered light that is created from the first light scattering from the inspection spot, and a second detector collecting a second scattered light that is created from the second light scattering from the inspection spot, wherein the first and second scattered lights are analyzed and classified according to defects positioned on the inspection spot of the object.

The light path changing member may include a first mirror passing the first portion of the main light to generate the first light and reflecting the second light to a second mirror, the second mirror reflecting the second light to a third mirror, the second mirror corresponding to the first mirror, the third mirror reflecting the second light to a fourth mirror, the third mirror being opposed to the second mirror, and the fourth mirror reflecting the second light onto the inspection spot, the fourth mirror being opposed to the first mirror and corresponding to the third mirror.

The apparatus may further include a first polarizer disposed on a path of the first light and including plates of about a ½ wavelength and about a ¼ wavelength to generate one light selected from the group consisting of a primary polarized (P) light, a secondary polarized (S) light and a circular polarized (C) light from the first light and a second polarizer disposed on a path of the second light and including plates of about a ½ wavelength and about a ¼ wavelength to generate one selected from the group consisting of a primary polarized (P) light, a secondary polarized (S) light and a circular polarized (C) light from the second light.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Figure 1:
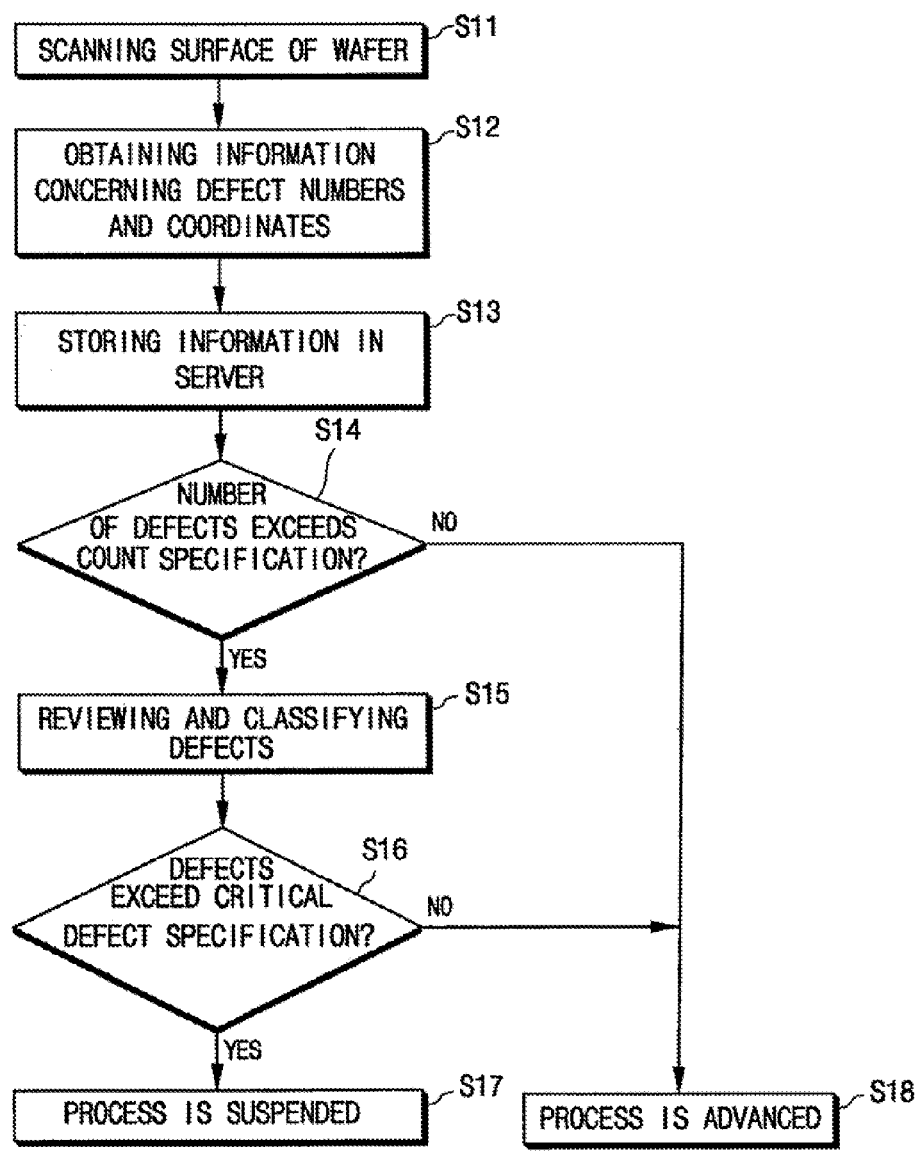
FIG. 1 is a flow chart illustrating a conventional method for detecting and classifying defects of an object.

Korean Patent Application No. 2003-12088, filed on Feb. 26, 2003, and entitled: "Method and Apparatus for Classifying Defects of an Object," is incorporated by reference herein in its entirety.

The present invention will now be described more fully hereinafter with reference to the accompanying drawings, in which preferred embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The Scattering Principle of the Polarized Light

By way of further background, when light is irradiated onto a plane of an object at a predetermined incident angle, the incident light is reflected from the plane of the object at a reflection angle substantially identical to the incident angle. When minute particles exist on the object, however, the incident light is scattered due to the particle.

When particles have spherical shapes, an intensity of the scattered light Is is represented by equation 1 according to an intensity of the incident light $I_i$.

$$I_s = (8\pi^4\alpha^6)/(\lambda^4 R^4) |(n^2-1)/(n^2+1)|^2 (1+\cos^2\theta) I_i \quad (1)$$

wherein, $\lambda$ represents a wavelength of the incident light, n represents a refractive index of a particle, R indicates a length from a position measuring the scattered light, i.e., a length of a detector, $\alpha$ indicates a diameter of the particle, and $\theta$ indicates the incident angle of the light.

Here, a diameter of the particle is smaller than the wavelength of the incident light $\lambda$. For example, a small particle has a diameter below approximately 0.5 µm and in equipment that utilizes an argon (Ar) laser, the wavelength of the incident light, i.e., the argon laser, is approximately 488 nm.

With respect to the term $(1+\cos^2\theta)$ in equation 1, the 1 indicates a term concerning an S light that is perpendicular to the plane of the object, and the $\cos^2\theta$ indicates a term concerning a P light that exists in the plane of the object.

Further, $I_s$ is inversely proportional to $\lambda^4$ and $R^4$, whereas $I_s$ is proportional to $\alpha^6$. In addition, Is is related to n and $I_i$.

Figure 3:
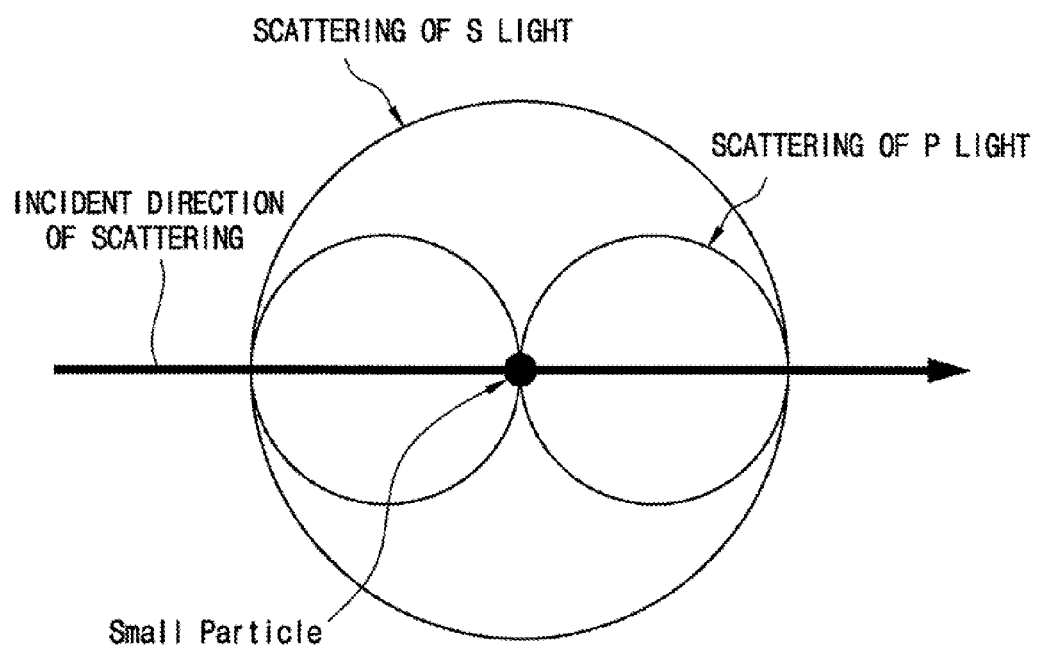
FIG. 3 illustrates a schematic plan view of a principle of a scattering of light in a spherical particle.

FIG. 3 is a schematic plan view illustrating the light scattered from the spherical particle.

Referring to FIG. 3, the intensity of the scattered light is varied according to the type of the polarization. The intensity of the scattered light is influenced by the incident angle ($\theta$), the wavelength ($\lambda$), the refractive index of the particle (n), the particle size, and the particle shape.

It is very difficult to calculate a quantity of scattered light from the particle in a real space. Since the inspection apparatus for the semiconductor process detects a particle and a micro-scratch on a wafer, the quantity of the scattered light is influenced by a structure, a property and a thickness of a lower layer as well as the shape, size and material of the particle.

According to a first embodiment of the present invention, defects on a wafer as a sample are classified using the scattering of polarized laser. Initial conditions for classifying the defects are shown in Table 1. Here, patterns are formed on the sample.

TABLE 1

| Light source | 488 nm Ar laser |
| --- | --- |
| Polarizer | ¼λ, ½λ plate |
| Polarized light | P light, S light, C light |
| Incident angle | about 20° from the plane |
| Detector | photo multiplier tube (PMT) |

A CMP process is performed on the wafer on which the particle and the micro-scratch are present. It is expected that the wafer includes defects, such as a particle, a micro-scratch, and polystyrene latex (PSL). The PSL generally has a spherical shape and is a typical sample of the particle.

The laser including the P light, the S light and the C light is irradiated onto the wafer. After the defects on the wafer are reviewed, the types of the defects are coded according to the respective characteristics of the defects. The intensity of the scattered light as a PMT voltage is measured.

Figure 4:
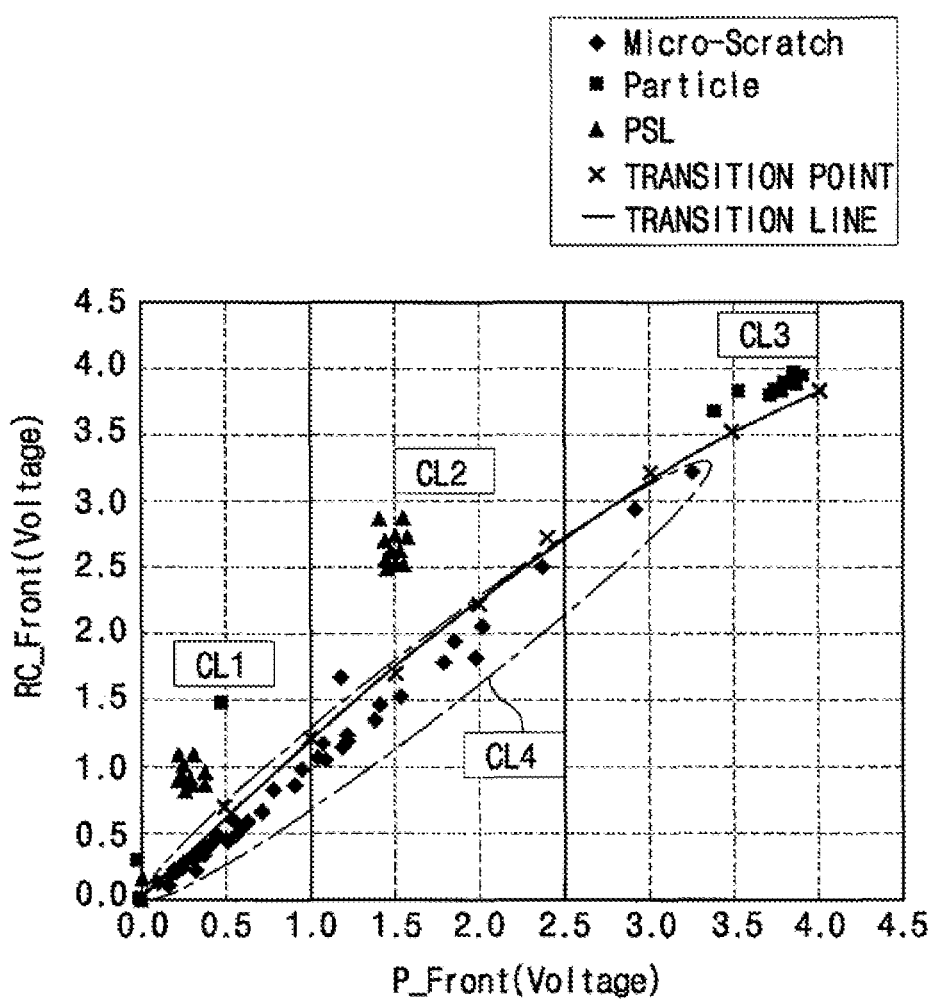
FIG. 4 is a graph showing a result concerning the defects according to a first embodiment of the present invention.

FIG. 4 is a graph illustrating a result concerning the defects according to the first embodiment of the present invention. FIGS. 5A to 5E are electronic microscope photographs illustrating the defects measured according to the first embodiment of the present invention.

The incident light includes combinations of the S-P lights, the P-C lights or the S-C lights. After the defect inspection process is executed using the combinations of the S-P lights, the P-C lights and the S-C lights, the combination of P-C lights is selected for its highest ability to classify various types of defects.

In FIG. 4, a horizontal X-axis indicates a PMT voltage of the P light, and a vertical Y-axis indicates a PMT voltage of the C light. The defects having higher PMT voltage are greatly scattered in a dark field, as shown in FIG. 4.

To classify the defects by size, a PSL having a diameter of approximately 0.2 µm to approximately 0.5 µm is deposited on the wafer.

Figure 5A:
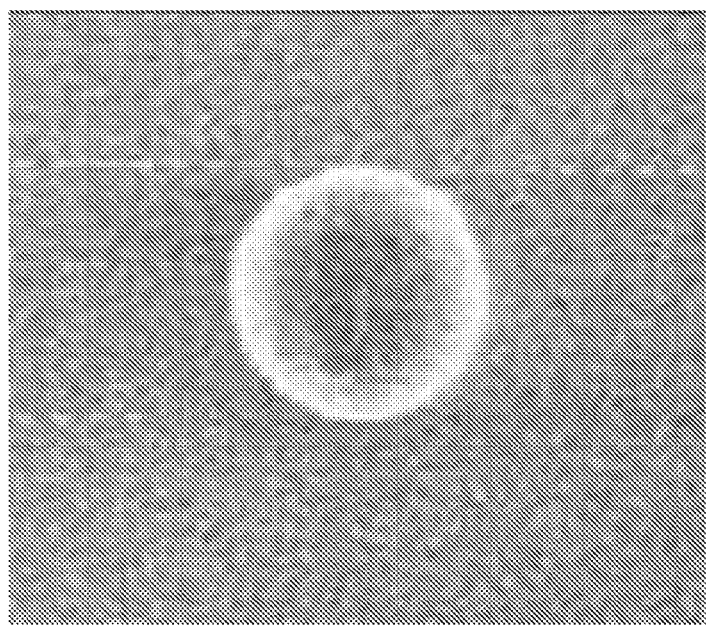
FIGS. 5A to 5E are electronic microscope photographs illustrating the defects measured according to the first embodiment of the present invention.
Figure 5B:
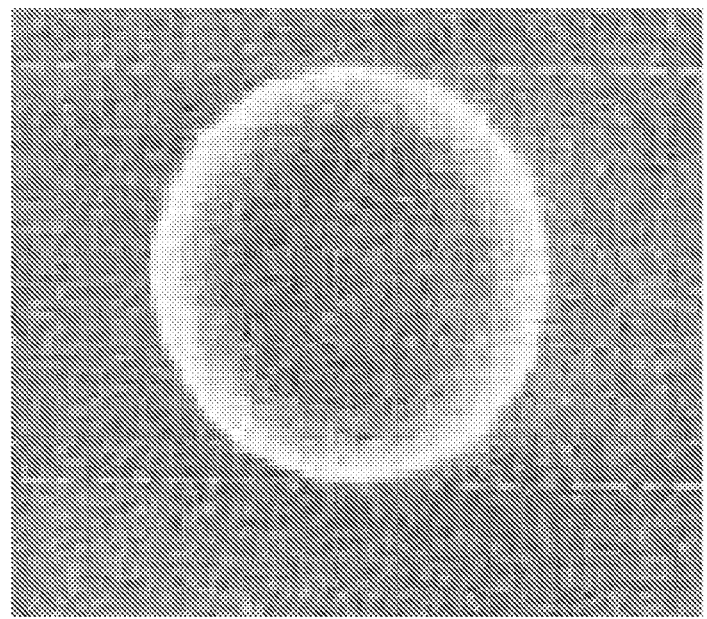
Figure 5C:
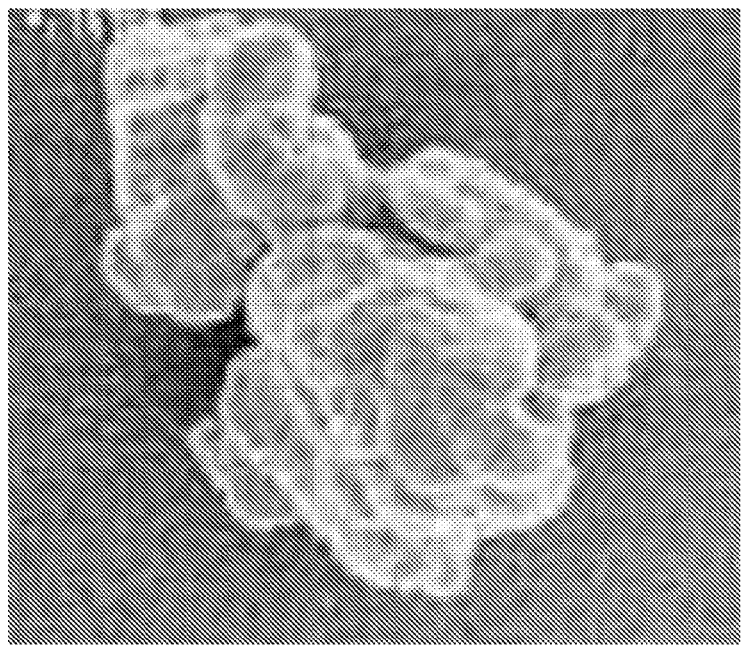
Figure 5D:
Figure 5E:
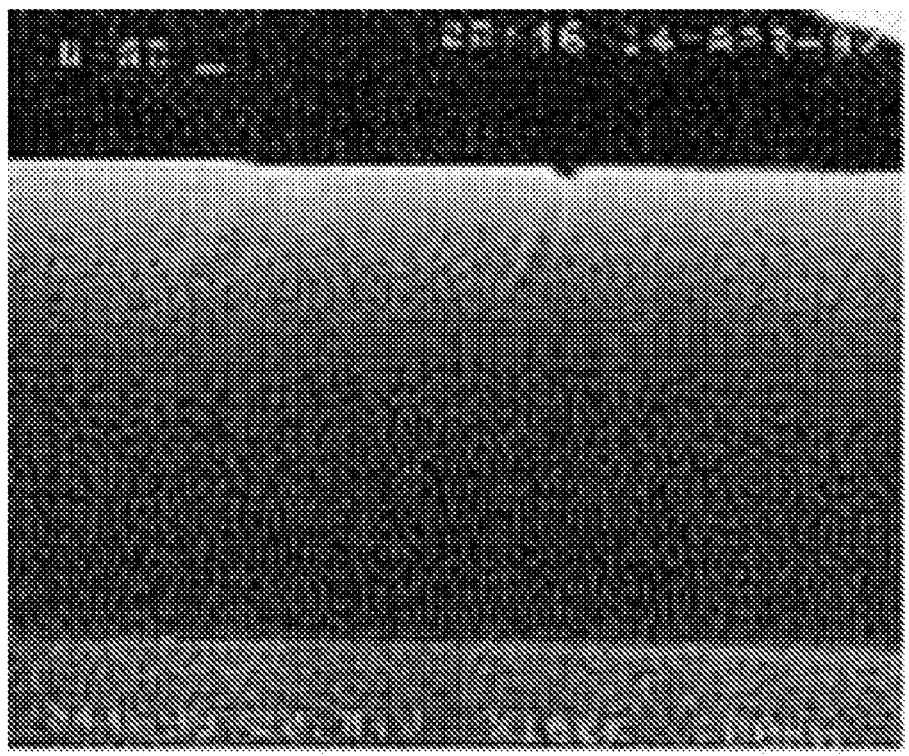

Referring to FIG. 4 and FIGS. 5A to 5E, a PSL having a diameter of approximately 0.2 µm, as shown in FIG. 5A, is formed in an area CL1, which has a P light PMT voltage of about 0.2 to about 0.5 and a C light PMT voltage of about 0.8 to about 1.2. A PSL having a diameter of approximately 0.5 µm, as shown in FIG. 5B, is formed in an area CL2, which has a P light PMT voltage of about 1.3 to about 1.7 and a C light PMT voltage of about 2.4 to about 2.9. The real particles having a diameter of approximately 2.0 µm, as shown in FIG. 5C, are formed in an area CL3, which has a P light PMT voltage of about 3.4 to about 4.0 and a C light PMT voltage of about 3.6 to about 4.0. In addition, a micro-scratch, as shown in FIGS. 5D and 5E, is formed in an area CL4, which is below a transition line and has a P light PMT of about 3.5.

The distribution of the defects determines the transition line, which is defined by equation 2:

$$Y = -0.0856X^2 + 1.2981X + 0.0096 \quad (2)$$

According to a result as shown in FIG. 4, it may be seen that the areas CL1 and CL2 formed by the PSL and the area CL3 formed by the real particles are positioned above the transition line, and the area CL4 formed by the micro-scratch is positioned below the transition line. Accordingly, the particle having projections and the micro-scratch without projections can be classified on the basis of the transition line.

It will be known that the signal distributions of the defect characteristics are different depending on two signals, i.e., the P light and the C light. When categories corresponding the signal ranges are defined and then each of the categories is stored in the inspection apparatus, the corresponding defects can be classified by the defined categories according to the signal distributions obtained during the inspection. Accordingly, the inspecting apparatus itself can determine and classify the defects without further reviewing. As a result, the present invention is able to advantageously identify the shape and size of a defect during inspection and before reviewing. In addition, the defects can be classified completely and rapidly regardless of the total number of defects.

The PMT voltage of the P light is higher than that of the C light in the PSL or the real particle. The PMT voltage of the P light is substantially identical to that of the C light in the micro-scratch. Thus, the classification of the defects using one of the P light and the C light is very difficult.

Figure 6:
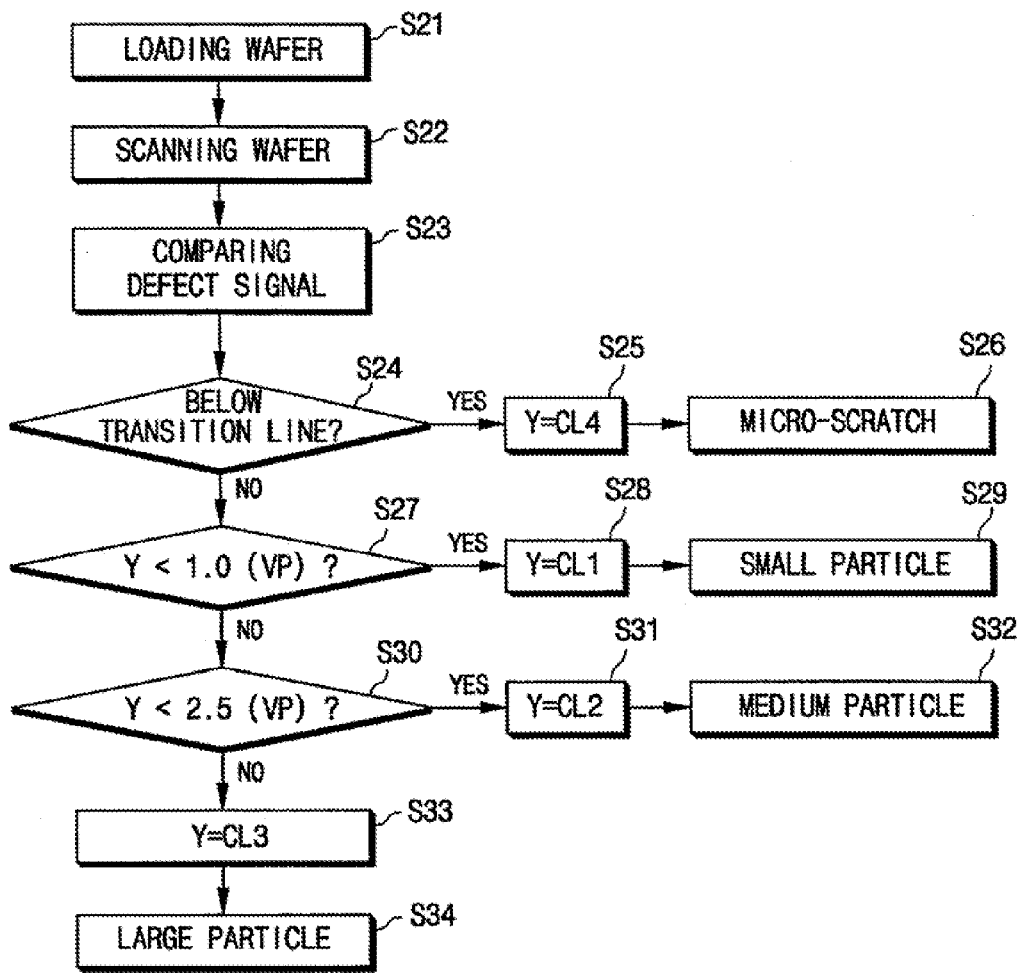
FIG. 6 is a flow chart illustrating a method for classifying defects according to the first embodiment of the present invention.

FIG. 6 is a flow chart illustrating a method for classifying defects according to the first embodiment of the present invention.

Referring to FIGS. 4 and 6, the defects are classified and set in the inspecting apparatus in accordance with their types by an automatic classification using the polarized lights.

In step S21, a wafer is loaded onto a stage. In step S22, the wafer on the stage is scanned using the P light and the C light. In step S23, the defect signals are compared. If the signals from the defects are distributed below the transition line in FIG. 4, as determined by step S24, these defects are determined to be in the area CL4, in step S25. Accordingly, in step S26, it is determined that these defects are micro-scratches.

To find the defects included in an area above the transition line, the PMT voltages of the P lights are compared with each other. As determined in step S27, if a particle has a PMT voltage of P light of less than about 1.0, these defects are determined to be in the area CL1, in step S28. Accordingly, in step S29, it is determined that these defects are small particles. As determined in step S30, if a particles has a PMT voltage of P light of about 1.0 to about 2.5, these defects are determined to be in the area CL2, in step S31. Accordingly, in step S32, it is determined that these defects are medium particles. As determined in step S30, if a particles has a PMT voltage of P light of greater than about 2.5, these defects are determined to be in the area CL3, in step S33. Accordingly, in step S34, it is determined that these defects are large particles.

Following Table 2 represents classification result of the defects according to this embodiment.

TABLE 2

| Defect No. | X-axis | Y-axis | PMT voltage of P light | PMT voltage of C light | Auto coding | Class |
| --- | --- | --- | --- | --- | --- | --- |
| 1 | 3.02 | 5.1 | 0.5 | 2.0 | CL1 | Small particle |
| 2 | 10.1 | 3.3 | 1.5 | 3.0 | CL2 | Medium particle |
| 3 | 5.2 | 25.6 | 2.0 | 3.0 | CL2 | Medium particle |
| 4 | 6.3 | 11.1 | 2.0 | 2.0 | CL4 | Micro-scratch |
| 5 | 44.2 | 2.1 | 2.0 | 1.8 | CL4 | Micro-scratch |
| 6 | 12.5 | 6.8 | 3.5 | 4.0 | CL3 | Large particle |
| . | . | . | . | . | . | . |
| . | . | . | . | . | . | . |
| . | . | . | . | . | . | . |
| 100 | 32.1 | 15.6 | 3.0 | 4.0 | CL3 | Large particle |

After an inspection, a review file is created in the inspecting apparatus. The review file determines coordinates of an X-axis and a Y-axis on the wafer corresponding to the defect numbers. The coordinates are utilized in finding the position of the desired defect for reviewing.

The PMT voltages of the polarized lights corresponding to the defect numbers, respectively, are stored. The PMT voltages are compared with each other so that the types of the defects are automatically coded. The types of defects are classified according to the auto-coded values.

The X-axis and the Y-axis may be set up relative to the S, P and C lights, and may be variously combined under different conditions. Although the defects are classified in accordance with the four types, the classes of the defects may not be restricted by means of these four types. The classes of the defects may be diversely set up depending on an inspector's choice.

Figure 7A:
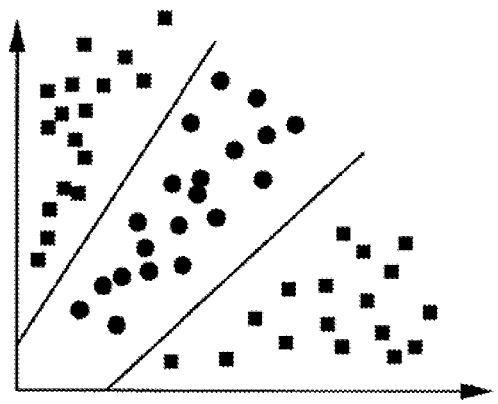
FIGS. 7A to 7C are graphs illustrating types of defects divided by a signal.
Figure 7B:
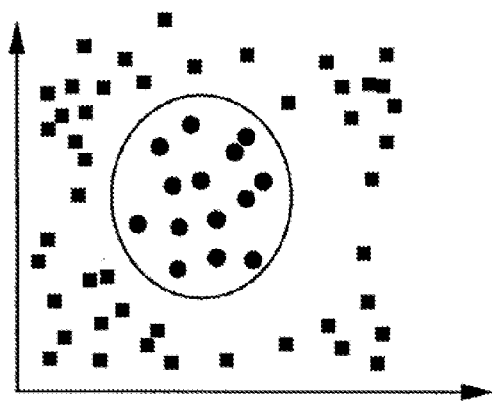
Figure 7C:
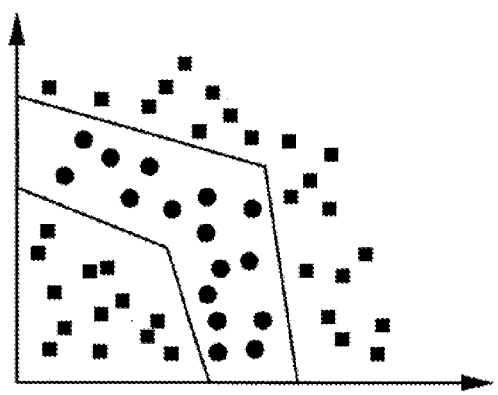
Figure 8A:
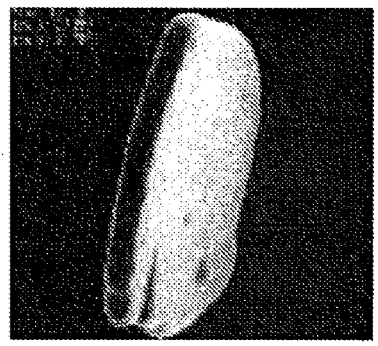
FIGS. 8A to 8C are electronic microscope pictures illustrating defects measured according to the first embodiment of the present invention.
Figure 8B:
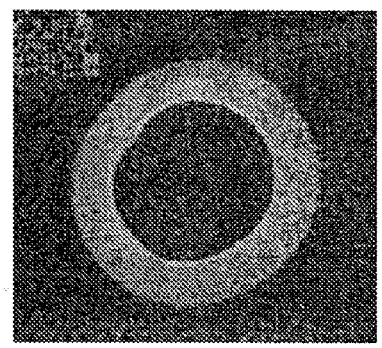
Figure 8C:
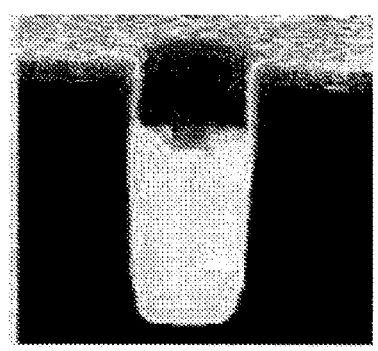

FIGS. 7A to 7C are graphs illustrating kinds of defects divided by a signal. FIGS. 8A to 8C are electronic microscope pictures illustrating defects measured in accordance with the first embodiment of the present invention.

At times, a size of a defect may not be accurately proportional to the PMT voltage, i.e. the scattering value. The reason for this discrepancy is that the scattering value from a large flat defect is lower than that from a small upright defect. The scattering value from the defect of FIG. 8A is often higher than that from the defect of FIG. 8B.

Furthermore, the scattering value is measured differently according to the shapes of the defects. Although the sizes of the defects gradually increase from the defect of FIG. 8C to the defect of FIG. 8A, the influence on the process growing gradually is lessened from the defect of FIG. 8C to the defect of FIG. 8A.

According to the first embodiment of the present invention, only the defect of FIG. 8C can be classified and managed in priority without reviewing.

Figure 9:
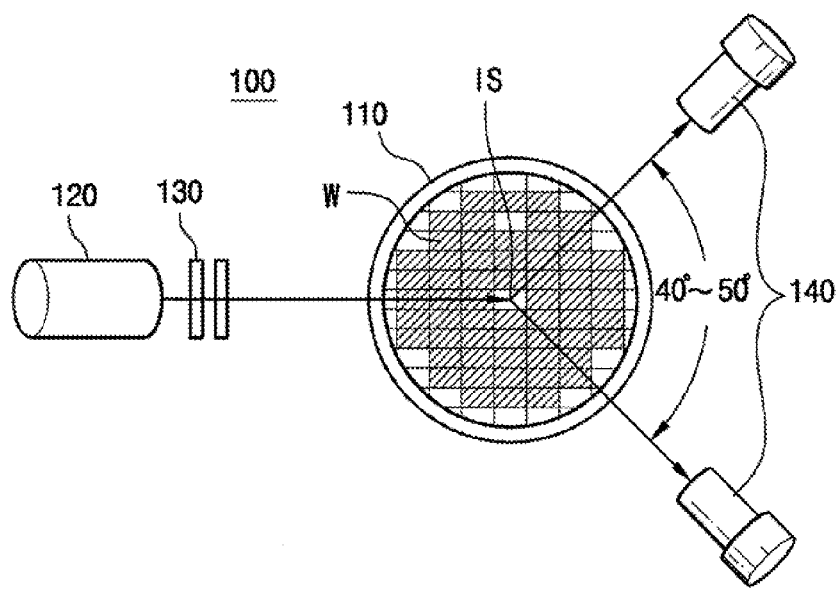
FIG. 9 illustrates a plan view of an apparatus for classifying defects according to a second embodiment of the present invention.
Figure 10:
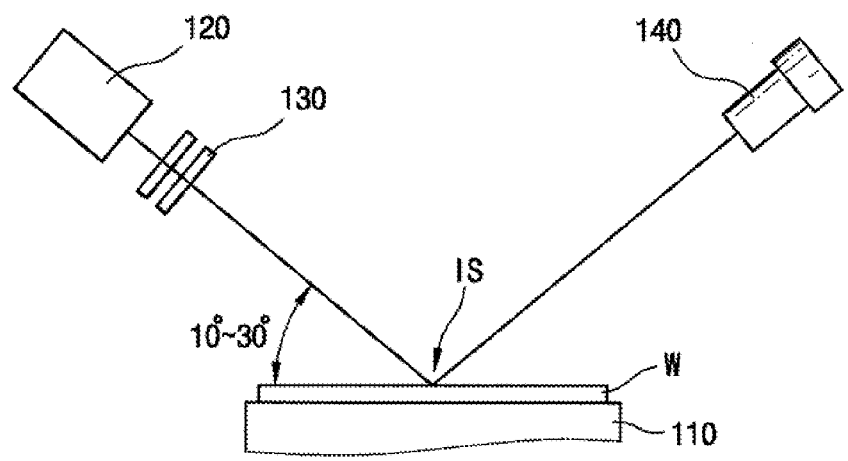
FIG. 10 illustrates a side view of the apparatus in FIG. 9.
Figure 11:
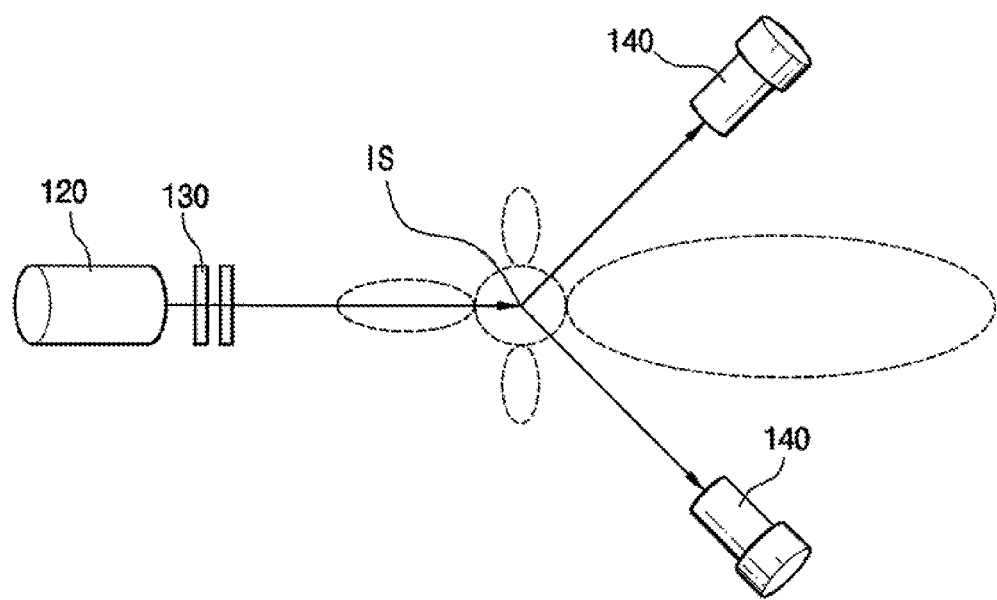
FIG. 11 illustrates a plan view of the scattering of a polarized light to explain a method for classifying defects according to the second embodiment of the present invention.
Figure 12:
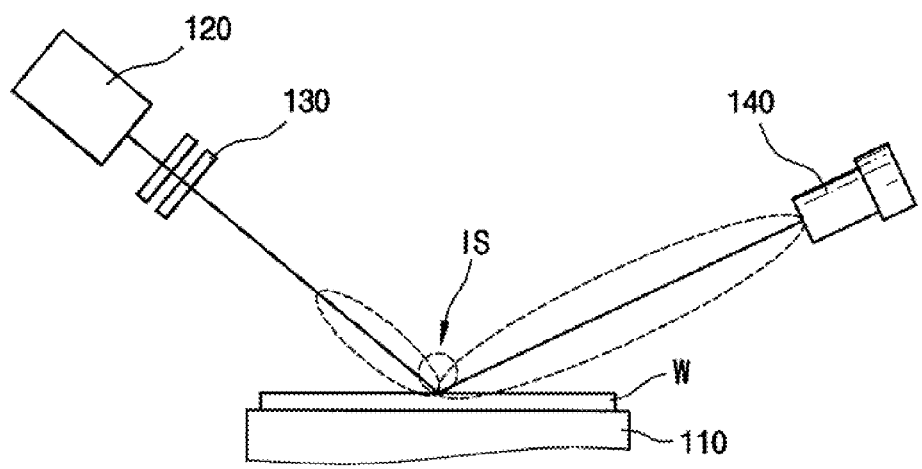
FIG. 12 illustrates a side view of the scattering of a polarized light to explain a method for classifying defects according to the second embodiment of the present invention.

FIG. 9 illustrates a plan view of an apparatus for classifying defects according to a second embodiment of the present invention. FIG. 10 illustrates a side view of the apparatus of FIG. 9. FIG. 11 illustrates a plan view of the scattering of a polarized light for explaining a method of classifying defects according to the second embodiment of the present invention. FIG. 12 illustrates a side view of the scattering of a polarized light for explaining a method of classifying defects according to the second embodiment of the present invention.

Referring to FIGS. 9 to 12, an apparatus 100 for classifying defects according to the second embodiment of the present invention, includes a stage 110 including a wafer W disposed thereon, a light source 120 emitting a light onto the wafer W to create an inspection spot IS on the wafer W, a polarizer 130 disposed on a path of the light between the wafer W and the light source 120 to polarize the light and to control the polarized light, and two detectors 140 disposed on either side of a traveling direction of the light at an angle of about 45° to collect the light scattered from the inspection spot.

The light source 120 is disposed at a slant with respect to a horizontal plane. The light emitted from the light source 120 is irradiated onto the wafer W at an incident angle of between about 10° and about 30°, and preferably at about 20°. The light source 120 preferably emits a laser having a wavelength of approximately 488 nm. The laser having this wavelength is suitable to defect inspection because the laser having the wavelength is stable. However, lasers or lights having other wavelength may be used for the defect inspection. The light from the light source 120 scans successively over the entire surface of the wafer W.

The polarizer 130 is disposed on a path of the light emitted from the light source 120. The polarizer 130 generates the P light, S light and C light. The polarizer 130 has a plate of about ½ wavelength or about ¼ wavelength and generates the polarized light by controlling the plate.

The polarized light passing through the polarizer 130 is reflected from the surface of the wafer or is scattered from the defects on the surface of the wafer. The inspection spot IS is created on the surface of the wafer where the light is irradiated. As shown in FIG. 9, when the defects exist on the inspection spot, the light is scattered from the defect so that a detector 140 located in a dark field detects the scattered light.

The detector 140 may include a PMT. The detector 140 measures the intensity of the scattered light, i.e., the PMT voltage. The two detectors 140 are disposed on either side of the inspection spot IS at an angle of about 4520 relative to the travel path of the light.

As shown in FIGS. 11 and 12, the laser is most powerfully reflected from the particles in spaces indicated by dot lines. The two detectors 140 are disposed at an angle of about 45° relative to the surface of the wafer to prevent the main light from interfering. Since a noise ratio relative to a reflecting signal of particle is extremely low in the range of about 40° to about 50°, the particles can be effectively detected without surface effects. Here, the necessary signal represents a peculiar signal from the particles. The noise signal represents a signal from patterns and roughness on the wafer excluding the defects.

FIG. 12 illustrates a side view of the scattering of a polarized light for explaining a method for classifying defects according to the second embodiment of the present invention. Particularly, FIG. 12 shows how to move the scattered light, when the polarized light is irradiated to the particle at an incident angle of about 20°. The detector 140 is disposed at an angle of about 10° to about 20° relative to the wafer W to collect the light scattered from the defects.

Figure 13:
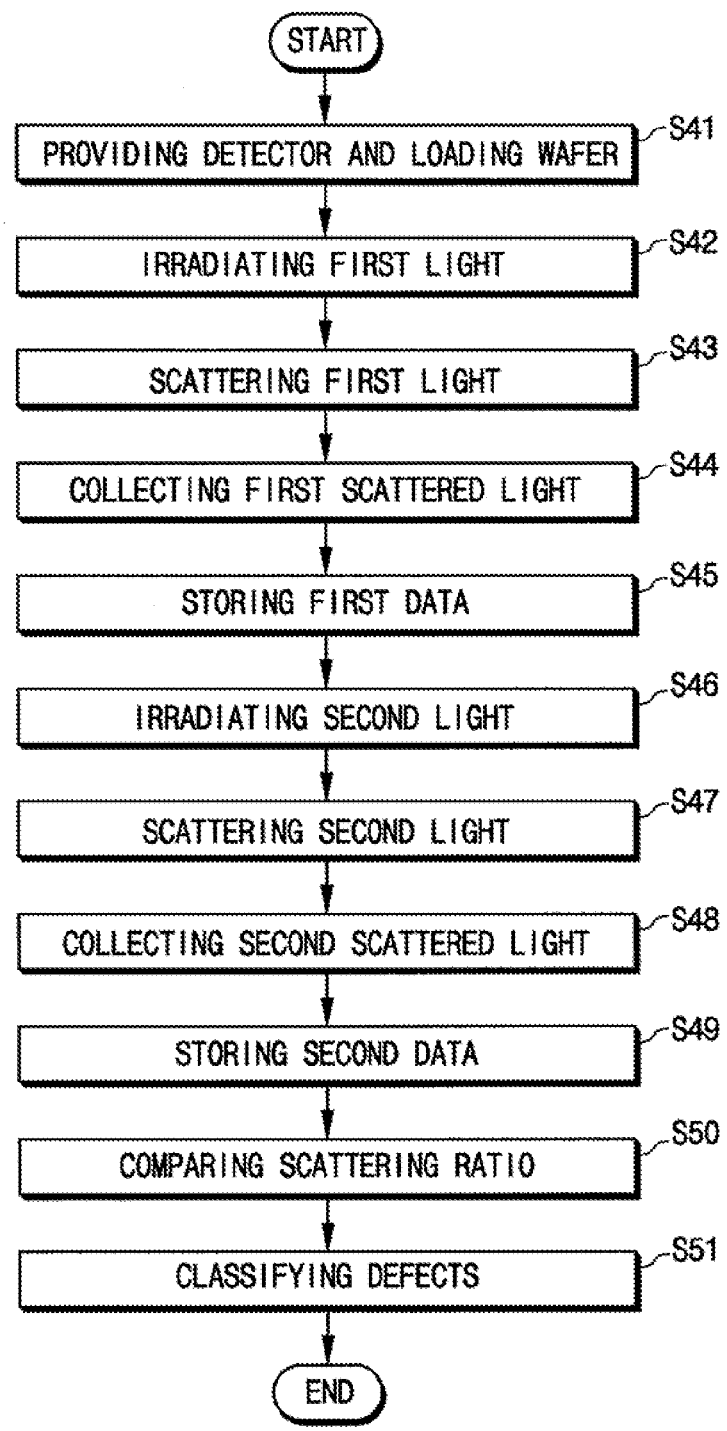
FIG. 13 is a flow chart illustrating a method for classifying defects according to the second embodiment of the present invention.

FIG. 13 is a flow chart illustrating a method for classifying defects according to the second embodiment of the present invention.

Referring to FIG. 13, in step S41, after the stage, the light source and the two detectors are provided with the inspecting apparatus, the wafer is loaded onto the stage. In step S42, the light source irradiates the first laser to the inspection spot on the wafer. In step S43, the irradiated light is reflected or scattered from the inspection spot on the wafer so that a first scattered light is created. In step S44, the PMT detector collects the first scattered light. In step S45, the PMT detector stores a first data concerning the collected first scattered light corresponding to the inspection spot in the server.

In step S46, the light source irradiates the second laser to the inspection spot on the wafer. In step S47, the irradiated light is reflected or scattered from the inspection spot so that a second scattered light is created. In step S48, the PMT detector collects the second scattered light. In step S49, the PMT detector stores a second data concerning the collected second scattered light corresponding to the inspection spot in the server.

In step S50, the scattering ratio of the inspection spot according to the first data and the second data is compared with each other. In step S51, the types of the defects are classified according to the signal of the inspection spot by using previously obtained sample values.

Conventionally, although the time of the reviewing may be varied according to the size of the wafer, working environment and processing condition, for example, the time required for reviewing one wafer is more than about 34 minutes, when the inspecting apparatus reviews the defects of the wafer having a number of about 1,020 and the time required for reviewing one defect is about two (2) seconds.

According to the inspecting apparatus of the present invention, the time required to scan a wafer is about three (3) minutes. Since the inspecting apparatus of the invention classifies the defects by scanning the wafer twice, the estimated time required for inspecting one wafer is about six (6) minutes.

Figure 2A:
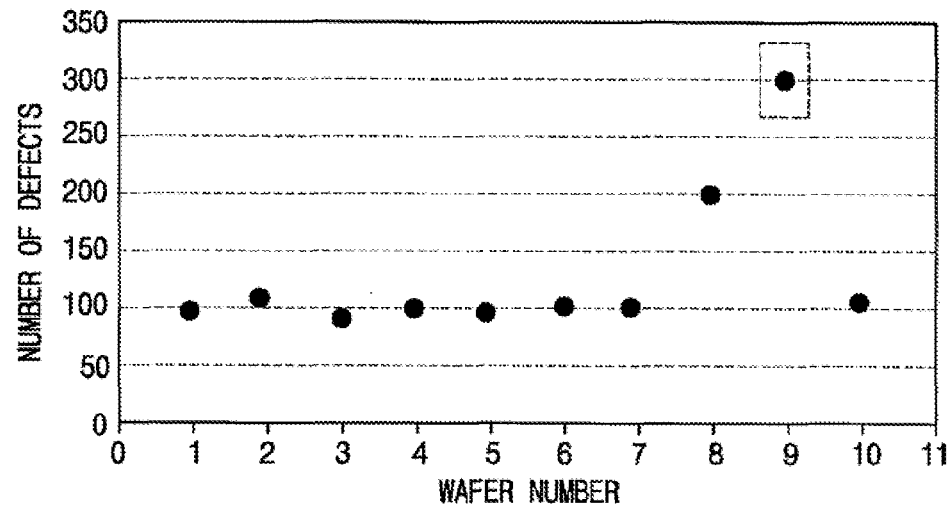
FIGS. 2A and 2B are graphs illustrating results of a conventional method for classifying the defects of the object.
Figure 2B:
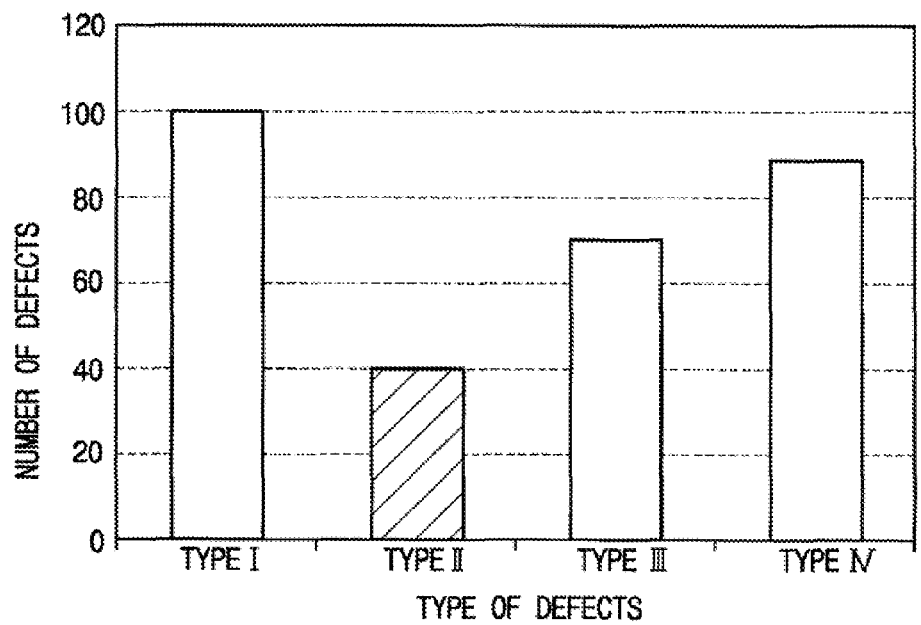
Figure 14:
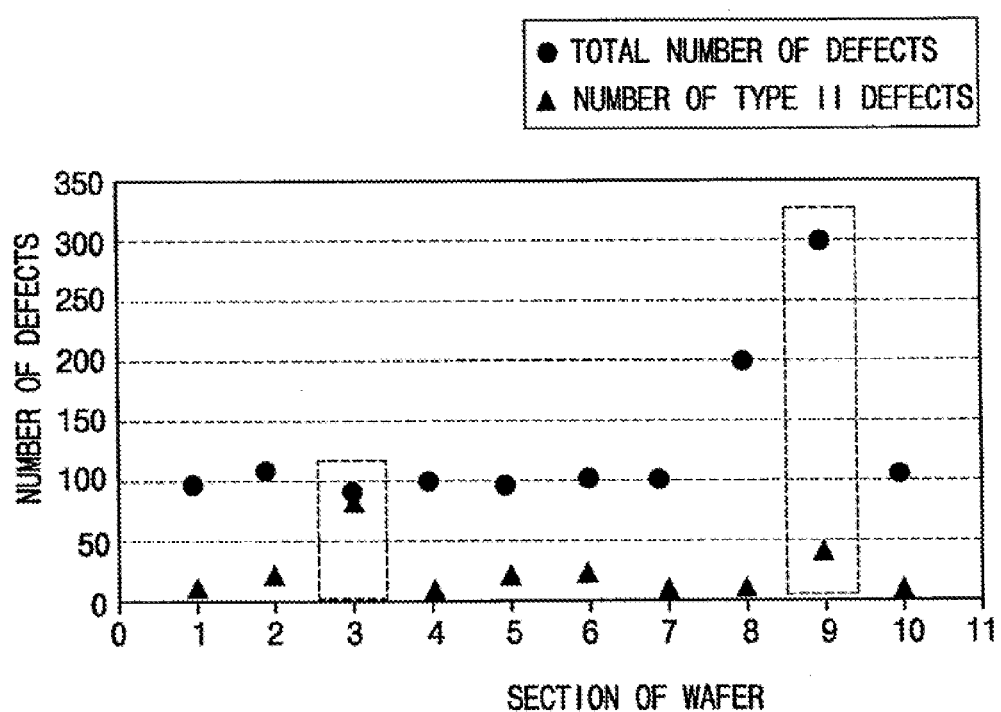
FIG. 14 is a graph illustrating classification result according to the second embodiment of the present invention.

FIG. 14 is a graph illustrating a result according to the second embodiment of the invention on condition identical to the experiments of FIGS. 2A and 2B.

Referring to FIG. 14, the total number of defects detected on the wafer and the number of type II defects are graphically shown in relation to a section on the wafer on which the defects are located. One section of the wafer, section No. 9, has a total number of defects of about 300. The number of defects in the No. 9 section is significantly higher than in any other section, each of the remaining sections having a total number of defects of about 100. The conventional apparatus reviews section No. 9 of the wafer.

However, the critical defect is identified as a type II defect. In general, the number of type II defects primarily determines the fabricating yield of semiconductor. According to the methods and the apparatuses of embodiments of the present invention, the number and the types of the defects on the wafer are simultaneously classified and also the number of the defects according to the types of the defects is simultaneously detected.

As may seen in FIG. 14, section No. 9 of the wafer has a relatively large number of type II defects, about 45. In addition, section No. 3 of the wafer has an even higher number of type II defects, about 80. In the conventional method, while section No. 3 of the wafer passes through the inspection process due the relative small number of total defects, section No. 9 of the wafer would be reviewed. Since the total number of defects and the types of defects are detected in the method according to the present invention, the inspecting apparatus according to the present invention can inspect and simultaneously classify the defects according to type. In addition, the inspecting apparatus of the present invention can inspect for critical defects. More specifically, the inspecting apparatus is able to monitor the number of critical defects regardless of the total number of defects. Furthermore, the inspecting apparatus extracts and inspects No. 3 section of the wafer, thereby improving the fabricating yield of the semiconductor. Since the scanning time of the invention is substantially identical to that of the conventional method in spite of the multitude of defects, a time delay for inspecting the wafer does not occur.

The method and the apparatus of the embodiments of the present invention have a further advantage with respect to a reduction of inspecting time. When the inspector classifies the defects in the semiconductor process line, the inspector cannot completely review all of the defects in the conventional method. When the total number of defects is greater than hundreds, the inspector randomly reviews some of the defects, typically no more than about 10% to about 20% of the total number of defects. The inspector classifies all of the defects by multiplying the selected defects by a constant multiple factor. Since an abnormal wafer may be identified as a normal wafer as a result of employing the conventional method, the fabricating yield may be lowered.

However, since the method and the apparatus of the embodiments of the present invention objectively determine and classify all of the defects, it is capable of precisely judging a quality of a process. For example, when two wafers are inspected, one wafer has about 1,000 defects and the other wafer has about 500 defects. While about one critical defect may exist in one wafer having about 1,000 defects, about 10 critical defects may exist in the other wafer having about 500 defects. The inspector cannot accurately determine and classify the above condition, because the inspector randomly selects and reviews the defects. Although the inspector reviews all of the defects, an accurate review is not possible due to the diminishing visual acuity of the inspector as the inspector's eyes become fatigued. However, in the present invention, although the wafer has hundreds or thousands defects, all of the defects can be inspected and classified without time delay.

Figure 15:
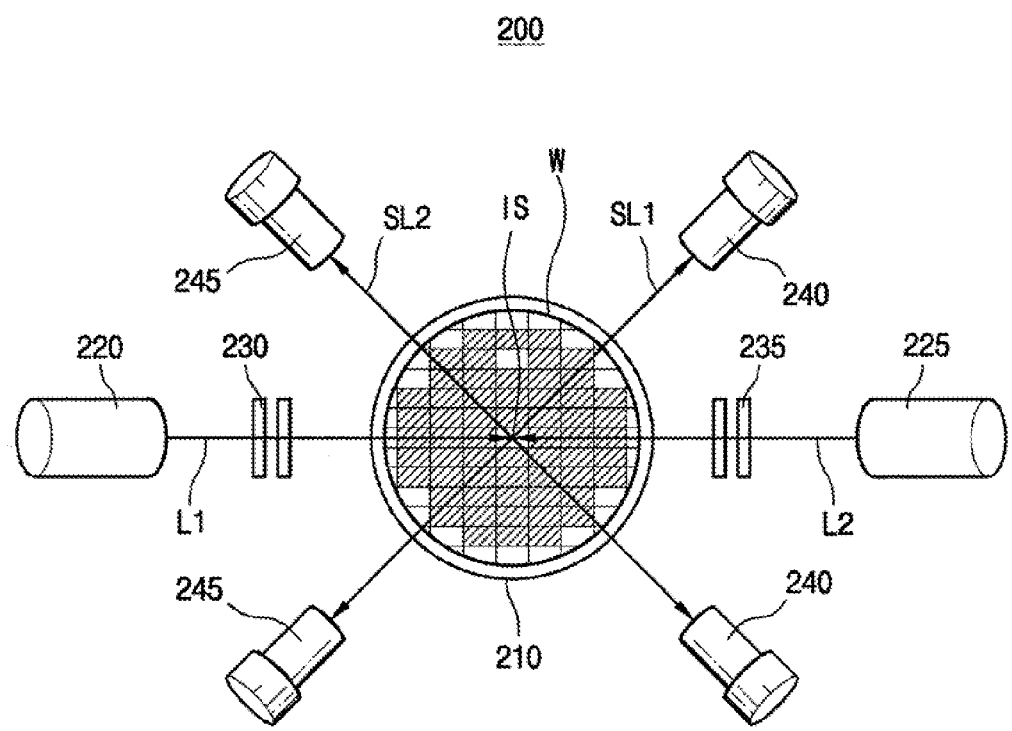
FIG. 15 illustrates a plan view of an apparatus for classifying defects according to a third embodiment of the present invention.
Figure 16:
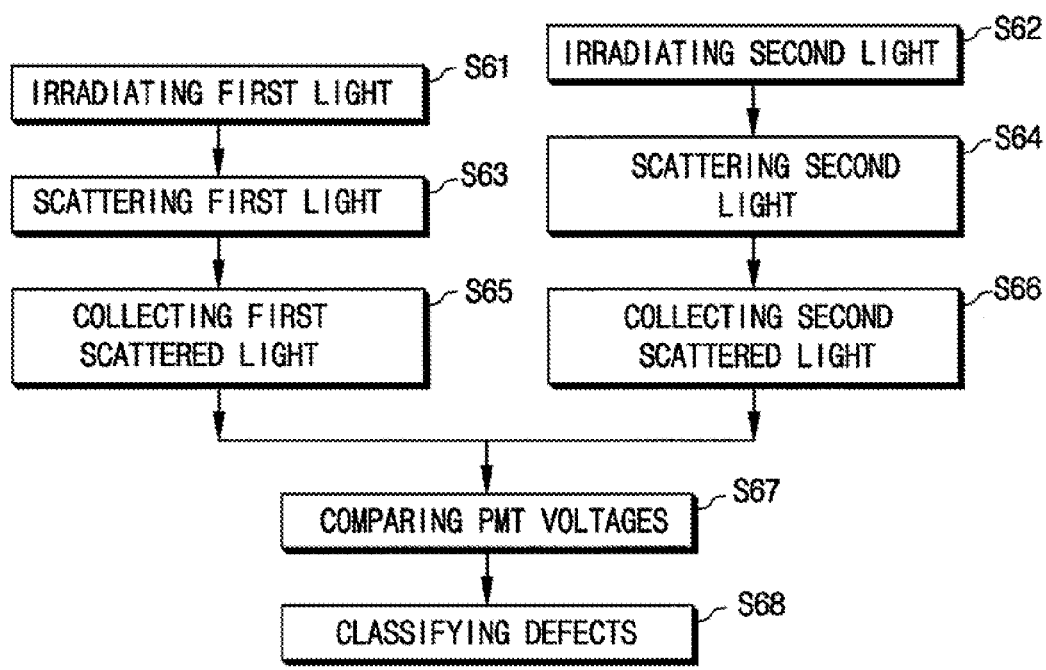
FIG. 16 is a flow chart illustrating a method for classifying defects according to the third embodiment of the present invention.

FIG. 15 illustrates a plan view illustrating an apparatus for classifying defects according to a third embodiment of the present invention. FIG. 16 is a flow chart illustrating a method for classifying defects according to the third embodiment of the present invention.

Referring to FIG. 15, an apparatus 200 for classifying defects includes a stage 210 having a wafer W disposed thereon, a first light source 220 emitting a first light L1 to the wafer W to create an inspection spot IS on the wafer W, a second light source 225 opposite to the first light source 220 and emitting a second light L2 to the inspection spot, a first polarizer 230 disposed on a path of the first light L1 between the wafer W and the first light source 220 to polarize the first light L1 and to control the polarized light, a second polarizer 235 disposed on a path of the second light L2 between the wafer W and the second light source 225 to polarize the second light L2 and to control the polarized light, two first detectors 240 disposed on either side of a traveling direction of the first light L1 at an angle of about 45° to collect a first light SL1 scattered from the inspection spot, and two second detectors 245 disposed on both sides of a traveling direction of the second light L2 at an angle of about 45° to collect a second light SL2 scattered from the inspection spot.

The first and second light sources 220 and 225 are disposed at a slant with respect to a horizontal plane, and are positioned to face each other at opposite sides of the wafer W. The first and second lights L1 and L2 emitted from the first and second light sources 220 and 225 are irradiated to the wafer W at an incident angle of about 20.degree. The first and second light sources 220 and 225 preferably emit lasers having a wavelength of approximately 488 nm. The laser having such a wavelength is suitable to defect inspection, in particular, because the laser is stable. However, lasers or lights having other wavelengths may be used for the defect inspection. The first and second lights L1 and L2 from the first and second light sources 220 and 225, respectively, successively scan over the entire surface of the wafer W. In addition, the first and second light sources 220 and 225 are separated from each other by an angle of about 180° in one embodiment. However, the first and second light sources 220 and 225 may be disposed at other angles as well, within the limit of having no fatal influence on the mutual functions.

A first polarizer 230 and a second polarizer 235 are disposed on the paths of the first and second lights L1 and L2. The first and second polarizers 230 and 235 generate the P light, S light and C light. The first and second polarizers 230 and 235 have plates of ½ wavelength or ¼ wavelength to generate the polarized lights by controlling the plates. It is preferred that the polarized lights are different each other to perform the method of the present invention.

The P light is created from the first polarizer 230. The P light is reflected from the surface of the wafer or is scattered from the defects on the surface of the wafer. An inspection spot IS is created on the surface of the wafer receiving the P light. As shown in FIG. 15, when the defects exist on the inspection spot IS, the P light is scattered from the defect so that the first detectors 240 located in a dark field detect the first scattered light SL1.

The first detectors 240 may include a PMT. The first detectors 240 measure the intensity of the first scattered light SL1, i.e., the PMT voltage. The first detectors 240 are disposed on either side of the inspection spot IS at an angle of about 45° relative to the travel path of the P light.

The C light is created from the second polarizer 235. The C light is reflected from the surface of the wafer or is scattered from the defects on the surface of the wafer. The C light is irradiated onto the inspection spot IS receiving the first light. Similar to the P light, when defects exist on the inspection spot, the C light is scattered from the defect so that the second detectors 245 located in a dark field detect the second scattered light SL2.

The second detectors 245 may include a PMT. The second detectors 245 measure the intensity of the second scattered light SL2, i.e., the PMT voltage. The second detectors 245 are disposed on either side of the inspection spot at an angle of about 45° relative to the travel path of the C light.

The P light and the C light are created from the first light and the second light, respectively, in one embodiment of the invention. However, the types of lights used in the present invention are not restricted to P light and C light. For example, alternate combinations of other polarized lights, such as a combination of P light and S light, a combination including S light, and a combination including C light, may be used in the present invention.

The first and second detectors 240 and 245 are disposed at an angle of about 45° relative to the surface of the wafer to prevent interference from the main light. Since a noise ratio relative to a reflecting signal of a particle is extremely low in the range of about 40° to about 50°, the particles can be effectively detected without interference from a surface effect. Here, the necessary signal represents a peculiar signal from the particles. The noise signal represents a signal from patterns and roughness on the wafer except for the defects.

The first and second lights L1 and L2 are irradiated to the particle at an incident angle of about 20°. The first and second detectors 240 and 245 are disposed at an angle of about 10° to about 20° relative to the wafer to collect the light scattered from the defects.

FIG. 16 is a flow chart illustrating a method for classifying defects according to the third embodiment of the present invention. In the above embodiment, after the scattered light of the P light from only one light source is measured, the scattered light of the C light is measured. However, in this third embodiment, the scattering values are simultaneously obtained by irradiating the P light and the C light to the same inspection spot using two light sources. Accordingly, the inspecting apparatus according to one embodiment of the present invention can simultaneously recall the reactivity of the two lights and also classify the defects.

Referring to FIG. 16, after the stage, the first and second light sources, and the first and second detectors are provided with the inspecting apparatus, the wafer is positioned on the stage. In step S61, the first light source 220 irradiates the first light L1 onto the inspection spot IS on the wafer. Simultaneously, in step S62, the second light source 225 irradiates the second light L2 onto the inspection spot IS. In step S63, after the first light L1 is changed into P light by passing through the first polarizer 230, and the P light is reflected or scattered from the inspection spot IS. Simultaneously, in step S64, after the second light L2 is changed into C light by passing the second polarizer 235, the C light is reflected or scattered from the inspection spot IS receiving the P light. In steps S65 and S66, the first and second detectors 240 and 245 collect the first scattered light SL1 and the second scattered light SL2, respectively. In step S67, after the PMT voltages of the defects relative to the P light and the C light are generated according to the first and second scattered lights SL1 and SL2, the PMT voltages are compared together. In step S68, the types of defects detected are classified according to the compared PMT voltages. After the inspecting apparatus measures the scattering value from the one inspection spot IS, the inspecting apparatus scans over the entire surface of the wafer by inspecting other inspection spots.

In the above embodiment, the time required to scan one wafer is about three (3) minutes. Since the inspecting apparatus classifies the defects by scanning the wafer twice, the estimated time required for inspecting one wafer is about six (6) minutes. Alternately, since the two light sources simultaneously irradiate the lights and the detectors additionally measure the polarized light in this third embodiment, the estimated time required for inspecting one wafer is about three (3) minutes.

Figure 17:
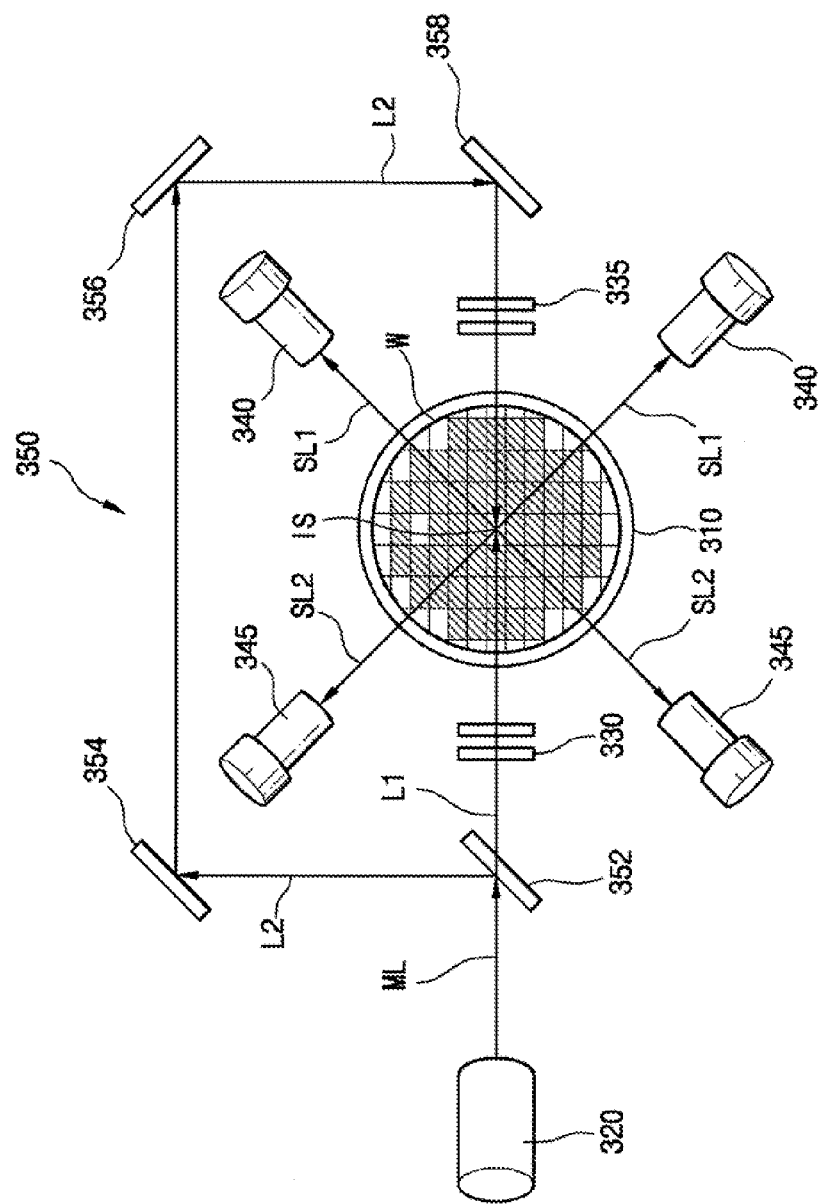
FIG. 17 illustrates a plan view of an apparatus for classifying defects according to a fourth embodiment of the present invention.

FIG. 17 illustrates a plan view of an apparatus for classifying defects according to a fourth embodiment of the present invention. In this fourth embodiment, a main light from one light source is divided into two lights using a light path-changing member. Thus, only the light path-changing member will described in connection with this embodiment of the present invention, and an extensive description of elements already described in connection with previous embodiments will be abbreviated or omitted.

Referring to FIG. 17, an apparatus 300 for classifying defects includes a stage 310 having a wafer W disposed thereon, a light source 320 emitting a main light ML to the wafer W to create an inspection spot IS on the wafer W, a light path changing member 350 passing a portion of the main light ML to create a first light L1 and changing a path of the remaining main light ML to create a second light L2, a first polarizer 330 disposed on a path of the first light L1 to polarize the first light L1 and to control the polarized light, a second polarizer 335 disposed on a path of the second light L2 to polarize the second light L2 and to control the polarized light, and two first detectors 340 disposed on either side of a traveling direction of the first light L1 at an angle of about 45° to collect a first light SL1 scattered from the inspection spot IS, and two second detectors 345 disposed on either side of a traveling direction of the second light L2 at an angle of about 45° to collect a second light SL2 scattered from the inspection spot IS.

The light path changing member 350 includes a first mirror 352 partially passing light therethrough to create the first and second lights L1 and L2, a second mirror 354 reflecting the second light L2, a third mirror 356 reflecting the second light L2 reflected from the second mirror 354, and a fourth mirror 358 reflecting the second light L2 reflected from the third mirror 356 to the inspection spot IS. The first, second, third and fourth mirrors 352, 354, 356 and 358 are disposed to form a rectangular shape. The first mirror 352 and the third mirror 356 are disposed on one diagonal of the rectangular shape. The second mirror 354 and the fourth mirror 358 are disposed on the other diagonal of the rectangular shape. More specifically, the light path changing member 350 divides the main light ML into the first light L1 and the second light L2 using the first mirror 352, and then changes the path of the second light L2 for directing the second light L2 toward the inspection spot IS parallel to the first light L1.

The main light ML preferably includes a laser having a wavelength of approximately 488 nm. The first and second lights L1 and L2 created by passing through the light path changing member 350 irradiated onto the wafer W at an incident angle of about 20° by first and second polarizers 330 and 350.

The first polarizer 330 is disposed on the path of the first light L1 between the first mirror 352 and the inspection spot IS. The second polarizer 335 is disposed on the path of the second light L2 between the fourth mirror 358 and the inspection spot IS. The first and second polarizers 330 and 335 create the P light, S light and C light. The first and second polarizers 330 and 335 have plates of ½ wavelength or ¼ wavelength to create the polarized lights by controlling the plates. It is preferred that the polarized lights are different from each other to perform the method of the present invention.

The P light is created from the first polarizer 330, and the C light is created from the second polarizer 335. The P light and the C light are scattered from the defects on the surface of the wafer, thereby creating the first and second scattered lights SL1 and SL2.

The P light and the C light may be created from the first and second lights in one embodiment of the invention. However, the types of lights used in the present invention are not restricted to P light and C light. Accordingly, alternate combinations of other polarized lights, such as a combination of P light and S light or a combination including S and C light may be used.

The first and second detectors 340 and 345 are disposed at an angle of about 450 relative to the incident direction of the first and second lights L1 and L2. Since a noise ratio relative to a reflecting signal of particle is extremely low in the range of about 40° to about 50°, the particles can be effectively detected without interference from a surface effect.

Since the inspecting apparatus can detect the number of the defects and classify the defects according to type in the present invention, the time required for a review process is decreased. Accordingly, the fabricating time of the semiconductor is significantly reduced.

In addition, the inspection apparatus can rapidly detect and classify numerous defects regardless of the total number of defects. The reliability of the inspecting result is additionally improved because all of the defects of the object are objectively identified.

Furthermore, a cost of the reviewing equipment is lowered by decreasing the dependence on the reviewing. Since the review process is automatically performed in the inspecting apparatus, a process line without a need for an inspector, i.e., human labor, may be designed.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method for identifying types of defects of an object, comprising:

irradiating first and second lights having different polarizations onto an inspection spot on the object;

collecting first and second scattered lights generated by the respective irradiated first and second lights scattering from the inspection spot;

identifying types of defects in the object based on the first and second scattered lights;

determining, based on the identified types of defects, whether the defects exceed a predetermined level; and altering a manufacturing process when the defects exceed the predetermined level, wherein identifying the types of defects includes:

identifying a first type of defect based on both the first scattered light and the second scattered light, and identifying a second type of defect based on only one of the first scattered light and the second scattered light.

2. The method as claimed in claim 1, wherein irradiating the first light and the second light comprises:
generating a first polarized light and a second polarized light from the first light and the second light, respectively, using a polarizer.

3. The method as claimed in claim 2, wherein the first polarized light and the second polarized light are two different polarizations selected from the group consisting of a primary polarized (P) light, a secondary polarized (S) light and a circular polarized (C) light.

4. The method as claimed in claim 1, further comprising:
providing a first light source for emitting the first light; and
providing a second light source for emitting the second light, wherein the second light source is positioned opposite to the first light source.

5. The method as claimed in claim 1, wherein irradiating the first light and the second light onto the inspection spot comprises:
irradiating a main light from a light source; and
generating the first light and the second light from the main light.

6. The method as claimed in claim 5, wherein the first light is directly generated from a first portion of the main light, and the second light is generated by changing a path of a second portion of the main light.

7. The method as claimed in claim 6, further comprising:
providing a light path changing member including a first mirror passing the first portion of the main light to generate the first light and reflecting the second light to a second mirror, the second mirror reflecting the second light to a third mirror, the third mirror reflecting the second light to a fourth mirror, and the fourth mirror reflecting the second light onto the inspection spot, the first, second, third, and fourth mirrors forming four points, respectively, of a rectangular path for the second light;
wherein the first light and the second light are generated from the main light using the light path changing member, and the second light is irradiated onto the inspection spot by being reflected from the first, second, third, and fourth mirrors.

8. The method as claimed in claim 7, wherein the second light reflected from the fourth mirror is irradiated onto the inspection spot from a direction opposite to a direction of the first light passing through the first mirror onto the inspection spot.

9. The method as claimed in claim 1, wherein a first polarized light and a second polarized light are generated using polarizers disposed on paths of the first light and the second light, respectively, and the first polarized light and the second polarized light are two different lights selected from the group consisting of a primary polarized (P) light, a secondary polarized (S) light and a circular polarized (C) light.

10. The method as claimed in claim 1, wherein the first and second lights having different polarizations are generated from a single light source.

11. The method as claimed in claim 1, wherein the first and second lights are irradiated onto an incident face of the object at an angle of about 10° to about 30° with respect to a surface of the incident face.

12. The method as claimed in claim 1, wherein the first and second scattered lights are collected at an angle in a range of about 40° to about 50° with respect to an irradiation direction of the first and second lights toward the inspection spot.

13. The method as claimed in claim 1, further comprising:
identifying a type of defect with respect to size.

14. An apparatus for identifying types of defects of an object, comprising:
light creating means configured to emit first and second lights having different polarizations on an inspection spot on the object;
a detecting member configured to collect first and second scattered lights that are created from the respective first and second lights scattering from the inspection spot; and
a classifier coupled to the detecting member, wherein:
the classifier is configured to identify a first type of defect in the object based on both the first scattered light and the second scattered light, and
the classifier is configured to identify a second type of defect in the object based on only one of the first scattered light and the second scattered light.

15. The apparatus as claimed in claim 14, wherein the light creating means comprises:
a light source; and
a polarizer disposed on a path between the light source and the inspection spot to create polarized light and to control characteristics of the polarized light.

16. The apparatus as claimed in claim 15, wherein the polarizer generates one or more of a primary polarized (P) light, a secondary polarized (S) light and a circular polarized (C) light.

17. The apparatus as claimed in claim 16, wherein the polarizer comprises at least one of a ½ wavelength plate and a ¼ wavelength plate to create the polarized lights by combining the plates.

18. The apparatus as claimed in claim 14, wherein the light creating means comprises at least one laser source for irradiating light onto the object within a range of angles of about 10° to about 30° with respect to a surface of the object.

19. The apparatus as claimed in claim 14, wherein the detecting member comprises:
at least one detector disposed above a surface of the object within a range of angles of about 40° to about 50° relative to a direction of light emitted toward the inspection spot.

20. A method for identifying types of defects of an object, comprising:
irradiating a first polarized light onto an inspection spot on the object;
collecting a first scattered light created by the first polarized light scattering from the inspection spot using a first detector;
irradiating a second polarized light onto the inspection spot;
collecting a second scattered light created by the second polarized light scattering from the inspection spot using a second detector;
identifying types of defects in the object based on the first and second scattered lights;
determining, based on the identified types of defects, whether the defects exceed a predetermined level; and
altering a manufacturing process when the defects exceed the predetermined level, wherein identifying the types of defects includes:
identifying a first type of defect based on both the first scattered light and the second scattered light, and
identifying a second type of defect based on only one of the first scattered light and the second scattered light.

21. The method as claimed in claim 20, wherein the first polarized light and the second polarized light are oppositely irradiated onto the inspection spot within a range of angles of about 10° to about 30° relative to an irradiated surface of the object.

22. The method as claimed in claim 20, wherein the first scattered light and the second scattered light are collected within a range of angles of about 40° to about 50° relative to irradiating directions of the first polarized light and the second polarized light toward the inspection spot.

23. The method as claimed in claim 20, wherein the first polarized light and the second polarized light are two different lights selected from the group consisting of a primary polarized (P) light, a secondary polarized (S) light and a circular polarized (C) light.

24. An apparatus for identifying types of defects of an object, comprising:
  a first light source configured to irradiate a first polarized light onto an inspection spot on the object;
  a first detector configured to collect a first scattered light that is created from the first polarized light scattering from the inspection spot;
  a second light source configured to irradiate a second polarized light onto the inspection spot;
  a second detector configured to collect a second scattered light that is created from the second polarized light scattering from the inspection spot; and
  a classifier coupled to the first and second detectors, wherein:
    the classifier is configured to identify a first type of defect in the object based on both the first scattered light and the second scattered light, and
    the classifier is configured to identify a second type of defect in the object based on a signal corresponding to only one of the first scattered light and the second scattered light.

25. The apparatus as claimed in claim 24, wherein the first light source and the second light source are disposed to face one another at opposite sides of the object and at a range of angles of about 10° to about 30° with respect to a surface of the object.

26. The apparatus as claimed in claim 24, wherein the first detector and the second detector are disposed above a surface of the object within a range of angles of about 40° to about 50° relative to irradiating directions of the first and second light sources toward the inspection spot.

27. The apparatus as claimed in claim 24, further comprising:
  a first polarizer disposed on a path of the first light source and including a ½ wavelength plate and a ¼ wavelength plate to generate one selected from the group consisting of a primary polarized (P) light, a secondary polarized (S) light and a circular polarized (C) light from the first light source; and
  a second polarizer disposed on a path of the second light source and including a ½ wavelength plate and a ¼ wavelength plate to generate a different one selected from the group consisting of the primary polarized (P) light, the secondary polarized (S) light and the circular polarized (C) light from the second light source.

28. A method for classifying defects of an object, comprising:
  irradiating a main light onto a light path changing member;
  creating a first polarized light and a second polarized light from light split from the main light;
  collecting a first scattered light created by the first polarized light scattering from an inspection spot on the object using a first detector;
  collecting a second scattered light created by the second polarized light scattering from the inspection spot using a second detector; and
  identifying types of defects in the object based on the first and second scattered lights;
  determining, based on the identified types of defects, whether the defects exceed a predetermined level; and
  altering a manufacturing process when the defects exceed the predetermined level, wherein identifying the types of defects includes:
    identifying a first type of defect based on both the first scattered light and the second scattered light, and
    identifying a second type of defect based on only one of the first scattered light and the second scattered light.

29. The method as claimed in claim 28, further comprising:
  providing a light path changing member including a first mirror passing a first portion of the main light and reflecting a second portion of the main light to a second mirror, the second mirror reflecting the second portion of the main light to a third mirror, the third mirror reflecting the second portion of the main light to a fourth mirror, and the fourth mirror reflecting the second portion of the main light onto the inspection spot, the first, second, third, and fourth mirrors forming four points, respectively, of a rectangular path for the second light,
  wherein the first portion of the main light and the second portion of the main light are generated from the main light using the light path changing member, and the second portion of the main light is irradiated onto the inspection spot by being reflected from the first, second, third, and fourth mirrors.

30. The method as claimed in claim 28, wherein the first polarized light and the second polarized light are created using polarizers disposed on a path of a first portion of the main light and on a path of a second portion of the main light, respectively, wherein the first polarized light and the second polarized light are two different lights selected from the group consisting of a primary polarized (P) light, a secondary polarized (S) light and a circular polarized (C) light.

31. An apparatus for identifying types of defects of an object, comprising:
  a light source configured to irradiate a main light;
  a light path changing member configured to pass therethrough a first portion of the main light and change a path of a second portion of the main light;
  a first polarizer configured to create a first polarized light from the first portion of the main light;
  a second polarizer configured to create a second polarized light from the second portion of the main light;
  a first detector configured to collect a first scattered light that is created from the first polarized light scattering from an inspection spot on the object;
  a second detector configured to collect a second scattered light that is created from the second polarized light scattering from the inspection spot; and
  a classifier coupled to the first and second detectors, wherein:
    the classifier is configured to identify a first type of defect in the object based on both the first scattered light and the second scattered light, and
    the classifier is configured to identify a second type of defect in the object based on a signal corresponding to only one of the first scattered light and the second scattered light.

32. The apparatus as claimed in claim 31, wherein the light path changing member comprises a first mirror passing the first portion of the main light and reflecting the second portion of the main light to a second mirror, the second mirror reflecting the second portion of the main light to a third mirror, the third mirror reflecting the second portion of the main light to a fourth mirror, and the fourth mirror reflecting the second portion of the main light onto the inspection spot, the first, second, third, and fourth mirrors forming four points, respectively, of a rectangular path for the second portion of the main light.

33. The apparatus as claimed in claim 31, further comprising:
   a first polarizer disposed on a path of the first portion of the main light and including a ½ wavelength plate and a ¼ wavelength plate to generate one light selected from the group consisting of a primary polarized (P) light, a secondary polarized (S) light and a circular polarized (C) light from the first portion of the main light; and
   a second polarizer disposed on a path of the second portion of the main light and including a ½ wavelength plate and a ¼ wavelength plate to generate a different one selected from the group consisting of the primary polarized (P) light, the secondary polarized (S) light and the circular polarized (C) light from the second portion of the main light.

34. The method as claimed in claim 1, wherein irradiating the first and second lights having different polarizations includes, in sequence, irradiating the first light having a first polarization onto the inspection spot, and irradiating the second light having a second polarization onto the inspection spot.

35. The method as claimed in claim 1, wherein identifying the first type of defect based on both the first scattered light and the second scattered light includes determining a distribution of the collected first and second scattered lights.

36. The method as claimed in claim 35, wherein determining the distribution of the collected first and second lights includes establishing a transition line.

37. The method as claimed in claim 1, wherein identifying the second type of defect based on only one of the first scattered light and the second scattered light includes determining that a defect corresponds to a first region of a distribution of one of the first scattered light and the second scattered light.

38. The method as claimed in claim 20, wherein identifying the first type of defect based on both the first scattered light and the second scattered light includes determining a distribution of the collected first and second scattered lights.

39. The method as claimed in claim 38, wherein determining the distribution of the collected first and second lights includes establishing a transition line.

40. The method as claimed in claim 20, wherein identifying the second type of defect based on only one of the first scattered light and the second scattered light includes determining that a defect corresponds to a first region of a distribution of one of the first scattered light and the second scattered light.

41. The method as claimed in claim 28, wherein identifying the first type of defect based on both the first scattered light and the second scattered light includes determining a distribution of the collected first and second scattered lights.

42. The method as claimed in claim 41, wherein determining the distribution of the collected first and second lights includes establishing a transition line.

43. The method as claimed in claim 28, wherein identifying the second type of defect based on only one of the first scattered light and the second scattered light includes determining that a defect corresponds to a first region of a distribution of one of the first scattered light and the second scattered light.

\* \* \* \* \*